United States Patent
Amar et al.

(10) Patent No.: US 7,504,647 B2
(45) Date of Patent: *Mar. 17, 2009

(54) METHOD AND APPARATUS FOR INSPECTING A SAMPLE HAVING A CONTROLLER FOR DETERMINING AN ESTIMATED HEIGHT OF THE DETECTOR FROM THE SAMPLE

(75) Inventors: Gal Amar, Peer Tuvia (IL); Avishay Guetta, Rehovot (IL); Doron Shoham, Rehovot (IL); Gilad Schwartz, Meishar (IL); Ronen Eynat, Shoham (IL)

(73) Assignee: Applied Materials, Inc., Santa Clara, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 11/466,314

(22) Filed: Aug. 22, 2006

(65) Prior Publication Data

US 2007/0034773 A1 Feb. 15, 2007

Related U.S. Application Data

(63) Continuation of application No. 10/877,311, filed on Jun. 25, 2004, now Pat. No. 7,115,890.

(60) Provisional application No. 60/523,376, filed on Nov. 18, 2003.

(51) Int. Cl.
*G01N 21/86* (2006.01)

(52) U.S. Cl. .................. 250/559.3; 250/201.2

(58) Field of Classification Search .............. 250/235, 250/234, 559.4, 548, 559.3, 221, 201.2, 559.38; 356/399–402
See application file for complete search history.

(56) References Cited

U.S. PATENT DOCUMENTS

| | | | | |
|---|---|---|---|---|
| 4,566,788 | A | * | 1/1986 | Buczek .................. 356/5.02 |
| 5,780,866 | A | | 7/1998 | Yamamura et al. |
| 2002/0001403 | A1 | | 1/2002 | Kikuchi |

FOREIGN PATENT DOCUMENTS

JP 2001134760 5/2001

OTHER PUBLICATIONS

Applied Materials Israel, LTD., International Search Report and Written Opinion, International Searching Authotity, PCT/US2004/020874 (Nov. 3, 2004).

* cited by examiner

*Primary Examiner*—Que T Le
(74) *Attorney, Agent, or Firm*—Tarek N. Fahmi

(57) ABSTRACT

Apparatus for optical inspection of a sample includes a detector assembly, which is configured to receive radiation from a focal area on the sample, and a translation mechanism, which is operative to impart motion to at least one of the detector assembly and the sample so that the focal area of the detector assembly translates over the sample along a translation path. A height sensor is positioned in a known location relative to the detector assembly so as to measure a height of the height sensor relative to a point on the sample that is ahead of the focal area by a predetermined distance along the translation path. A controller is adapted to determine an estimated height of the detector assembly, responsively to the height measured by the height sensor along the translation path.

8 Claims, 3 Drawing Sheets

METHOD AND APPARATUS FOR INSPECTING A SAMPLE HAVING A CONTROLLER FOR DETERMINING AN ESTIMATED HEIGHT OF THE DETECTOR FROM THE SAMPLE

CROSS-REFERENCE TO RELATED APPLICATION

This application is a Continuation of U.S. application Ser. No. 10/877,311 Jun. 25, 2004, U.S. Pat. No. 7,115,890, which claims the benefit of U.S. Provisional Patent Application No. 60/523,376, filed Nov. 18, 2003, whose disclosure is incorporated herein by reference.

FIELD OF THE INVENTION

The present invention relates generally to optical inspection, and specifically to methods and apparatus for automatic focus adjustment during scanning of a solid-state surface by an optical inspection system.

BACKGROUND OF THE INVENTION

Maintaining proper focus of objective optics can be critically important in high-resolution optical inspection systems, such as those used in production of semiconductor devices. Most inspection systems use auto-focus mechanisms based on optical sensing methods. Optical auto-focus sensing has the advantage that the quality of the optical focus can be sensed within the focal area of the optics without interfering substantially with the image capture function of the optics. For some applications, however, optical sensing may not provide sufficient focal precision, due, for example, to color variations on the inspected surface or to local height variations in the surface that are too small for the auto-focus system to track.

Other, non-optical types of non-contact position sensors are also known in the art. For example, Lion Precision, of Saint Paul, Minnesota, produces a line of capacitive sensors, which may be used in micro-positioning. These sensors are capable of making position readings with high bandwidth and tracking precision of 0.1 µm or less. A disadvantage of these sensors, however, is that they are optically opaque, and therefore cannot generally be used to make measurements in the focal area of an optical system without blocking at least part of the field of view of the optics.

The use of capacitive position sensors in automated focus adjustment of optical inspection systems has been described in the patent literature. For example, U.S. Patent Application Publication US 2002/0001403 A1, whose disclosure is incorporated herein by reference, describes a method for automatically focusing an ultraviolet objective lens, using a capacitance sensor near the objective lens. The capacitive sensor is used to measure a distance between the objective lens and an object under inspection, and the objective lens or object is moved based on the result of the measurement.

As another example, U.S. Patent Application Publication US 2002/0067477 A1, whose disclosure is incorporated herein by reference, describes the use of a capacitance-type sensor disposed near an objective lens to detect the distance between the objective lens and a semiconductor wafer under inspection. The focusing of the optical imaging system is adjusted by driving a moving stage vertically until the distance between the objective lens and the semiconductor wafer becomes optimal.

SUMMARY OF THE INVENTION

In some embodiments of the present invention, an optical inspection system comprises a detector assembly and a focus adjustment mechanism that is based on one or more non-optical sensors. Typically, the detector assembly comprises an optical detector, such as an image sensor array, and objective optics, which form an image on the detector of an area of a sample under inspection. (The area of the sample whose image is captured by the detector assembly at a given point in time is referred to herein as the "focal area.") The non-optical sensors typically comprise height sensors, such as capacitive sensors, which are positioned in fixed, known locations alongside the detector assembly. Each height sensor measures its own respective height relative to a point below it on surface of the sample. The focus adjustment mechanism adjusts the focus of the image formed by the objective optics according to the heights measured by the one or more height sensors.

Since the height sensors make their height measurements relative to points outside the focal area of the detector assembly, in embodiments of the present invention the focus adjustment mechanism takes into account the displacement between the focal area and the height measurement points. For this purpose, in some embodiments, two or more height sensors are disposed on opposing sides of the detector assembly. The focus adjustment mechanism combines the height readings of the sensors to estimate the actual height of the detector assembly relative to the focal area on the sample surface. For this purpose, the focus adjustment mechanism may take an arithmetic average of the height readings. Alternatively, other estimation techniques may be used, such as second- or higher-order curve fitting, in order to estimate and compensate for the curvature of the sample surface. The focus adjustment mechanism typically makes special provision for height estimation when imaging areas near the edges of the sample, at which the height reading of at least one of the height sensors may be invalid.

In some embodiments of the present invention, a translation mechanism moves either the detector assembly or the sample, or both, so that the focal area of the detector assembly scans over the sample along a translation path in a selected scanning pattern. The height sensor or sensors are positioned so that at least one of the height sensors measures its height relative to a point on the sample that is ahead of the focal area of the detector assembly on the translation path. The focus adjustment mechanism uses the reading of the height sensor to "look ahead" by a predetermined distance along the scan path. In other words, the focus of the image at each point along the translation path is adjusted based on the height measured a short time earlier by the height sensor when the height sensor was located over the same point on the translation path.

In some of these embodiments, the scanning pattern comprises a raster scan, and the translation path comprises multiple parallel scan lines in the raster. Typically, the translation mechanism scans over successive lines of the raster pattern in opposite (zigzag) directions. Two height sensors are disposed alongside the detector assembly, one on either side along the scan axis, so that one of the sensors gives a height reading at a point ahead of the focal area of the detector assembly in each scan direction.

There is therefore provided, in accordance with an embodiment of the present invention, apparatus for optical inspection of a sample, including:

detector assembly, which is configured to receive radiation from a focal area on the sample;

a translation mechanism, which is operative to impart motion to at least one of the detector assembly and the sample so that the focal area of the detector assembly translates over the sample along a translation path;

a height sensor, positioned in a known location relative to the detector assembly so as to measure a height of the height sensor relative to a point on the sample that is ahead of the focal area by a predetermined distance along the translation path; and a controller, which is adapted to determine an estimated height of the detector assembly, responsively to the height measured by the height sensor along the translation path.

In some embodiments, the apparatus includes a focus adjustment mechanism, which is operative to adjust a focus of the detector assembly, responsively to the estimated height. Typically, the focus adjustment mechanism is adapted to apply the estimated height in order to adjust the focus after a predetermined time during which the translation mechanism has scanned the focal area to the point at which the height was measured. Additionally or alternatively, the focus adjustment mechanism is adapted to apply the height measured at the point in order to adjust the focus after the focal area has translated over the sample by the predetermined distance.

In some embodiments, the height sensor includes a first height sensor, which is positioned in a first known location on a first side of the detector assembly and measures a first height relative to a first point on the sample, and the apparatus includes a second height sensor, which is positioned in a second known location on a second side of the detector assembly, opposite the first side, so as to measure a second height relative to a second point on the sample. Typically, the controller is operative to determine the estimated height responsively to the first and second heights. In one embodiment, the controller is adapted to determine the estimated height responsively to an average of the first and second heights.

In some of these embodiments, the translation mechanism is adapted to cause the focal area to scan over the sample along a plurality of scan lines in a raster pattern, such that the focal area scans along at least some of the scan lines in a first direction, in which the first point is ahead of the focal area, and the focal area scans along other ones of the scan lines of the raster pattern in a second direction, in which the second point is ahead of the focal area. Typically, the controller is adapted to determine the estimated height responsively to the first height on the at least some of the scan lines, and responsively to the second height on the other ones of the scan lines.

In disclosed embodiments, the translation mechanism is adapted to cause the focal area to scan over the sample along a plurality of scan lines in a raster pattern. Typically, at least one of the scan lines extends beyond an edge of the sample, such that at a beginning of the at least one of the scan lines, the height sensor is positioned to measure the height of the height sensor in proximity to the edge of the sample while the focal area of the detector assembly remains at least partially beyond the edge, and wherein the controller is adapted to store the height measured by the height sensor in proximity to the edge and to determine the estimated height at the beginning of the at least one of the scan lines responsively to the stored height.

Typically, the detector assembly includes at least one detector and optics, which are configured to form an image of the focal area on the at least one detector. In some embodiments, the height sensor includes a non-optical sensor, typically a capacitive sensor. In a disclosed embodiment, the optics have a collection angle, and the height sensor is tilted so as to measure the height in proximity to the focal area without blocking the collection angle. In an exemplary embodiment, the sample includes a semiconductor wafer.

There is also provided, in accordance with an embodiment of the present invention, apparatus for optical inspection of a sample, including:

a detector assembly, which is configured to receive radiation from a focal area on the sample;

first and second height sensors, positioned in known locations relative to the detector assembly so as to measure respective first and second heights of the first and second height sensors relative to respective first and second points on the sample on opposing sides of the focal area; and a controller, which is adapted to determine an estimated height of the detector assembly, responsively to the first and second heights measured by the first and second height sensors.

In a disclosed embodiment, the controller is adapted to determine the estimated height responsively to an average of the first and second heights.

In another embodiment, the apparatus includes a translation mechanism, which is operative to impart motion to at least one of the detector assembly and the sample so that the focal area of the detector assembly translates over the sample along a translation path, and the controller is adapted to determine a curvature of the sample responsively to multiple readings of the first and second heights measured at multiple points along the translation path, and to determine the estimated height responsively to the curvature. Typically, the controller is adapted to determine the curvature by performing a spline fit to the multiple readings of the first and second heights.

In a further embodiment, the apparatus includes at least third and fourth height sensors, which are positioned relative to the detector assembly so that the first, second, third and fourth height sensors surround the focal area.

In some embodiments, the apparatus includes a translation mechanism, which is operative to impart motion to at least one of the detector assembly and the sample so that the focal area of the detector assembly scans over the sample along one or more scan lines, wherein the first and second points are disposed on the scan lines, so that on each of the scan lines, one of the first and second points is ahead of the focal area, and another of the first and second points is behind the focal area. Typically, at least one of the scan lines extends beyond an edge of the sample, to a location at which the first height sensor is unable to provide a valid measurement of the first height, and the controller is adapted to store the first height measured by the first height sensor in proximity to the edge and to determine the estimated height at the location responsively to the stored first height. In one embodiment, the controller is adapted to determine an offset value responsively to a difference between the first and second heights measured in proximity to the edge, and to determine the estimated height at the location at which the first height sensor is unable to provide the valid measurement of the first height responsively to the second height measured by the second height sensor at the location and to the offset value.

There is additionally provided, in accordance with an embodiment of the present invention, a method for optical inspection of a sample, including:

receiving radiation at a detector assembly from a focal area on the sample;

translating the focal area over the sample along a translation path;

positioning a height sensor in a known position relative to the detector assembly so as to measure a height of the height sensor relative to a point on the sample that is ahead of the focal area by a predetermined distance along the translation path; and determining an estimated height of the detector assembly responsively to the height measured by the height sensor along the at least some of the scan lines of the raster pattern.

There is further provided, in accordance with an embodiment of the present invention, a method for optical inspection of a sample, including:

receiving radiation at a detector assembly from a focal area on the sample;

positioning first and second height sensors in known locations relative to the detector assembly so as to measure respective first and second heights of the first and second height sensors relative to respective first and second points on the sample on opposing sides of the focal area; and determining an estimated height of the detector assembly responsively to the first and second heights measured by the first and second height sensors.

The present invention will be more fully understood from the following detailed description of the embodiments thereof, taken together with the drawings in which:

DETAILED DESCRIPTION OF EMBODIMENTS

Figure 1:
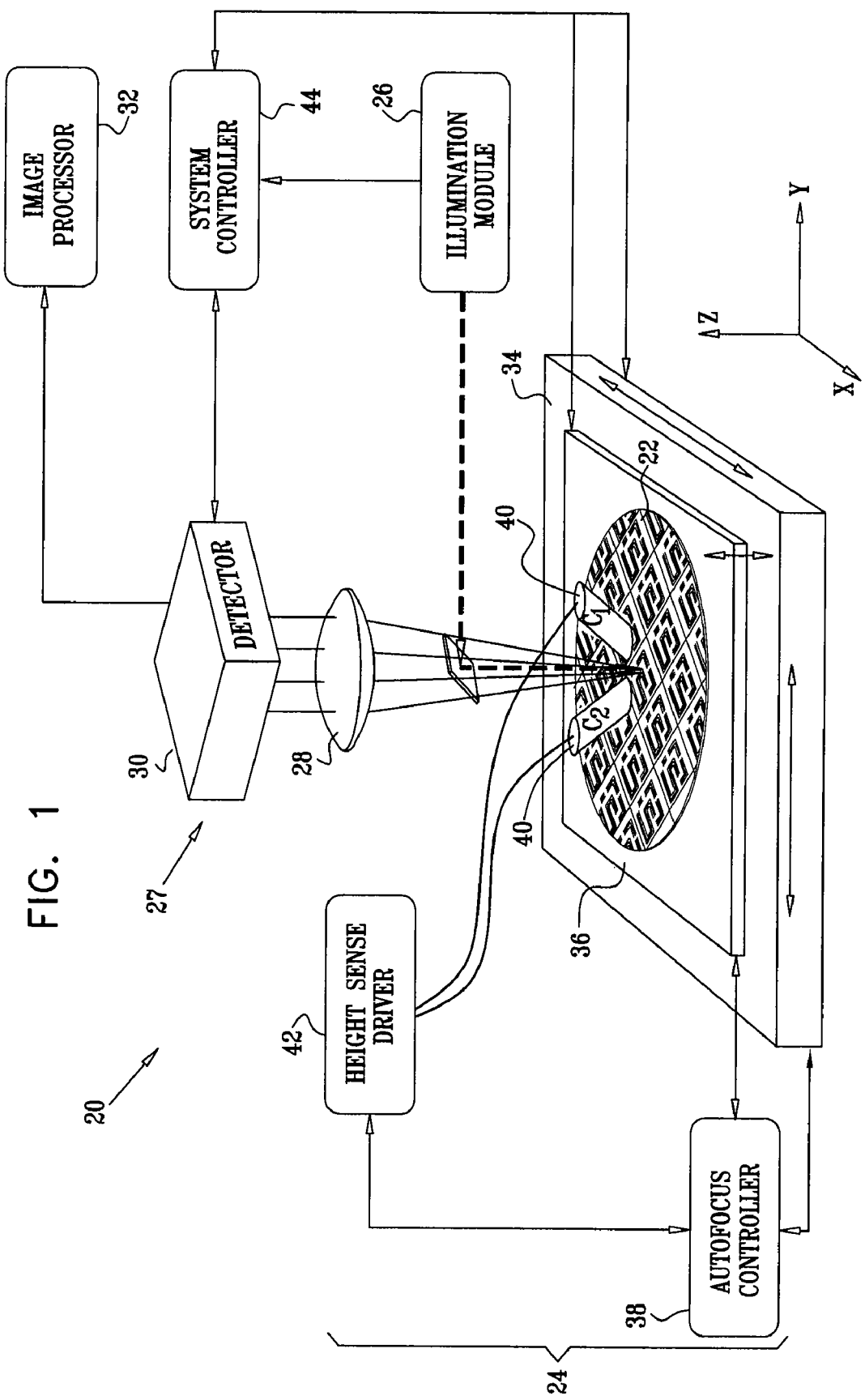
FIG. 1 is a schematic, partly pictorial illustration of an optical inspection system, in accordance with an embodiment of the present invention.

FIG. 1 is a schematic, pictorial illustration of a system 20 for optical inspection of a sample, such as a semiconductor wafer 22, in accordance with an embodiment of the present invention. System 20 comprises an autofocus mechanism 24, whose design and operation are described in detail hereinbelow. Although this subsystem is described here, by way of example, in the context of a wafer inspection system, it may similarly be applied in optical inspection systems of other sorts—including both bright-field and dark-field inspection systems—for inspection not only of semiconductor wafers, but also of samples of other types.

System 20 comprises an illumination module 26, which illuminates an area on wafer 22 with either pulsed or continuous illumination. The illumination may be in the visible, infrared or ultraviolet range of the spectrum, or may include radiation in two or more of these ranges simultaneously. A detector assembly 27 captures an image of the illuminated area of the wafer. The area of the wafer surface whose image is captured by the detector assembly is referred to herein as the focal area of the detector assembly. Signals generated by detector assembly 27 are processed by an image processor 32, typically in order to detect defects on wafer 22 or to assess other surface features.

Typically, detector assembly 27 comprises objective optics 28 and at least one detector 30. The detector typically comprises an image sensor array, and objective optics 28 form a magnified image on the array of the focal area of the wafer surface. In one embodiment, detector 30 comprises multiple image sensor arrays, and optics 28 are configured to form respective images on the arrays of the radiation scattered from the focal area into different, respective angular ranges. Detector assemblies of this sort are described in detail in U.S. patent application Ser. No. 06/415,082 filed 30 Sep. 2002, PCT application WO2004031754, PCT application WO2004031753 and PCT application WO2004031741 which are assigned to the assignee of the present patent application and whose disclosures are incorporated herein by reference. Alternatively, system 20 may comprise other types of illumination modules and detector assemblies, such as a flying-spot laser scanner and detector. (Note that in systems using flying-spot-type illumination, the focal plane is determined by the illumination optics, and hence the autofocus mechanism described below should be configured to control the height of the wafer relative to the illumination optics, rather than relative to the detector assembly.)

The focal area of detector assembly 27 is generally much smaller than the total area of wafer 22 that is to be inspected. Therefore, wafer 22 is typically mounted on a translation stage 34, which serves as a translation mechanism to scan the wafer in a raster pattern relative to the detector assembly. Alternatively, the translation mechanism may be adapted to move the detector assembly, or to move both the detector assembly and the wafer, or to optically scan the focal area of the detector assembly over the wafer surface. In the description that follows, for convenience and clarity, the plane of wafer 22 is taken to be the X-Y plane, and the parallel scan lines of the raster scan are assumed to be aligned in the Y-direction. Typically, to maximize the throughput of system 20, stage 34 scans over successive lines of the raster pattern in opposite (zigzag) directions. Alternatively, the translation mechanism in system 20 may comprise a rotation stage, which scans wafer 22 in a circular or spiral pattern. Further alternatively, the translation mechanism may cause detector assembly 27 to scan over the wafer in any other suitable pattern known in the art. Scanning and other operations in system 20 are coordinated by a system controller 44.

Autofocus mechanism 24 comprises an elevation stage 36, which raises and lowers wafer 22 (in the Z-direction) under the command of an autofocus controller 38. Stage 36 typically comprises a precision motorized stage, which is capable of fixing the vertical position of the wafer to within about 1 µm. Such stages are commercially available, for example, from Physik Instrumente (Karslruhe, Germany). Alternatively, a piezoelectric stage may be used if finer vertical positioning is required. Further alternatively or additionally, the autofocus controller may raise and lower the detector assembly or may change the distance between optics 28 and detector 30 (or may change the distance between elements of optics 28 in order to adjust the focal plane location).

Capacitive height sensors 40 (labeled $C_1$ and $C_2$) are used to determine the proper focus adjustment for each image along the scan. Each height sensor generates a voltage that is proportional to its distance from the surface of wafer 22. Sensors 40 are fixed to the detector assembly to either side of the focal area. In one embodiment, the lower surfaces of sensors 40 are located about 0.5 mm from the wafer surface and are capable of measuring height variations within a range of about ±50 µm, with a tracking accuracy of about ±0.1 µm and high bandwidth (typically up to 20 kHz). Height variations of the surface may occur, for example, due to unevenness or bowing of the wafer under inspection. Since the heights of sensors 40 are fixed and calibrated relative to optics 28, any short-term variation in the voltage outputs of sensors 40 is indicative of a corresponding change in the distance between the optics and the surface of wafer 22. (Sensor drift may cause long-term variations, which are typically calibrated out of the readings, as described further hereinbelow.) A height sense driver 42 receives and processes the voltage readings provided by sensors 40, in order to provide one or more height inputs to autofocus controller 38.

Although the embodiments described herein use capacitive height sensors, other types of non-contact sensors may be used to similar effect. For example, sensors 40 may comprise inductive distance sensors, or non-optical precision distance sensors of other types, as are known in the art. Aspects of the present invention may also be adapted for use with optical focus sensors.

Figure 2A:
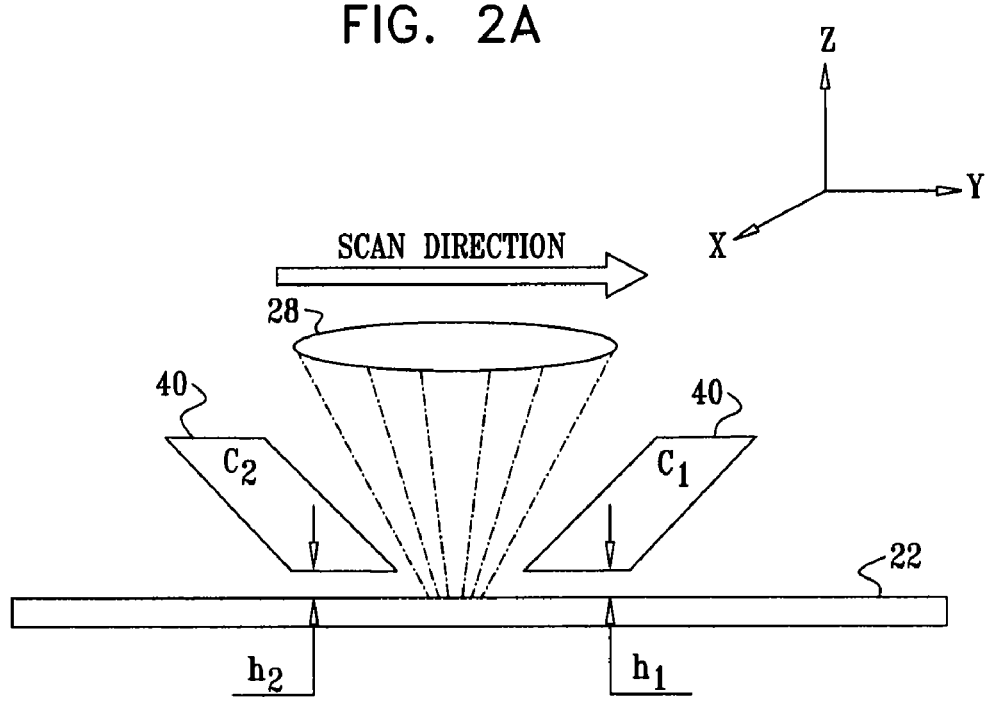
FIG. 2A is a schematic side view of objective optics and height sensors used in an optical inspection system, in accordance with an embodiment of the present invention.
Figure 2B:
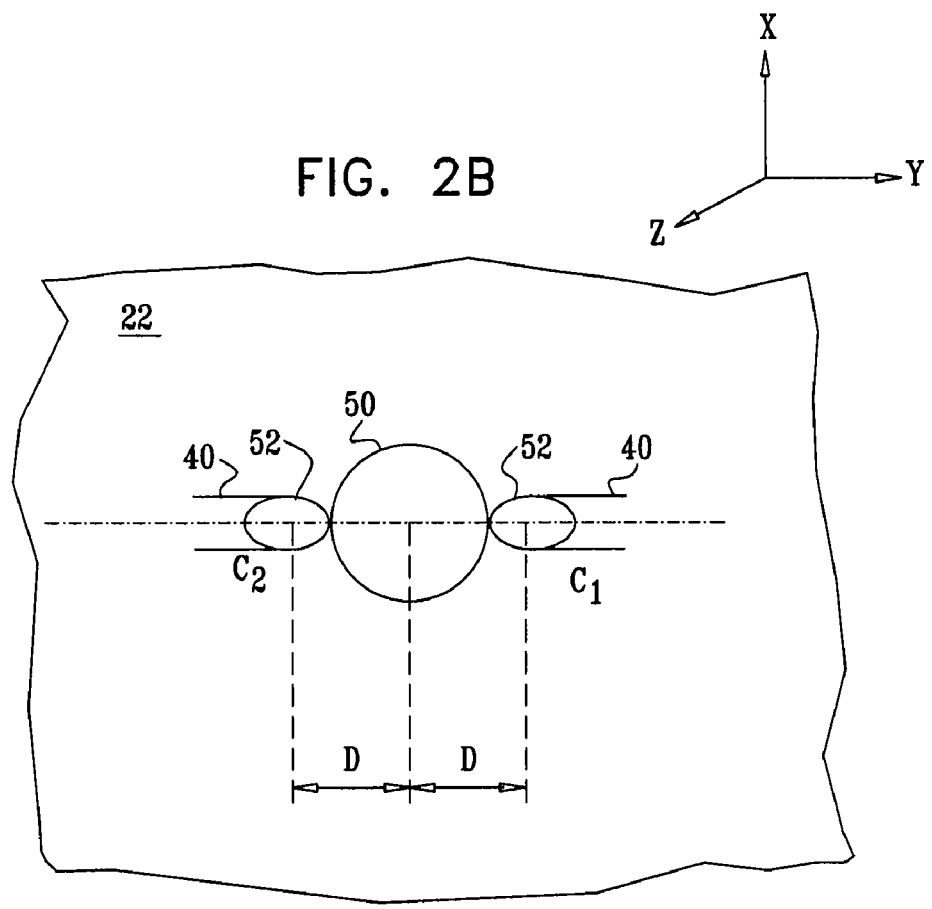
FIG. 2B is a schematic top view of a sample under inspection, showing an area of an image captured by an optical inspection system and adjacent height sensing areas, in accordance with an embodiment of the present invention.

Reference is now made to FIGS. 2A and 2B, which show details of objective optics 28 and height sensors 40, in accordance with an embodiment of the present invention. FIG. 2A is a side view of the height sensors and optics, while FIG. 2B is a top view of the surface of wafer 22, showing focal area 50 and "footprints" 52 of the height sensors. These footprints represent the approximate area of the wafer surface that influences the capacitance measured by each of the sensors, and hence determine the height readings. The height sensors $C_1$ and $C_2$ measure their respective heights, $h_1$ and $h_2$, with respect to the wafer surface at the center points of the footprints, which are displaced by a distance D along the Y-axis from the center of the focal area. As noted above, $h_1$ and $h_2$ in system 20 are typically on the order of 0.5 mm, and may vary over a range of ±50 µm over the surface of wafer 22.

The bodies of height sensors 40 may be tilted, as shown in FIG. 2A, so as to permit footprints 52 to approach focal area 50 in close proximity to the focal area without blocking the collection angle of optics 28. As a result, footprints 52 are elliptical, rather than round. Due to physical constraints imposed by the construction and operation of height sensors 40, the height readings provided by the sensors are actually averaged over the footprint areas. Typically, for capacitive height sensors of sufficient sensitivity and accuracy, footprints 52 are each about 3 mm long by 2 mm wide, and the centers of the footprints are displaced by D=8 mm from the center of focal area 50. The footprints are slightly larger than the actual dimensions of the sensors. The averaged nature of the height sensor readings is advantageous in that it tends to smooth over small, local height variations that are not useful to autofocus mechanism 24. On the other hand, if any part of footprint 52 of either of sensors 40 is not entirely on the surface of wafer 22, the height readings provided by that sensor may be invalid. This problem is addressed further hereinbelow with reference to FIG. 3.

Autofocus controller 38 uses the readings of sensors 40 (as provided by height sense driver 42) to determine a feedback control parameter h, which is indicative of the height of optics 28 relative to the wafer surface. The autofocus controller then drives stage 36 so as to zero out any variations in h, so that optimal focus is maintained over the entire scan of wafer 22. A number of different operational modes may be used in determining the parameter h:

Single sensor control—In this mode of operation, the autofocus controller simply chooses one of sensors 40 and assumes that the readings of that sensor are indicative of the present height of optics 28 relative to wafer 22. This approach has the advantage of simplicity, but is susceptible to error due to local height variations over the distance D between sensor footprint 52 and focal area 50. Therefore, this mode is typically not used in system 20 except possibly in edge regions in which the height readings of one or both sensors are invalid.

Look-ahead control—The height reading of the height sensor that is ahead of focal area 50 along the current Y-direction scan line is predictive of the height of optics 28. In the example shown in FIGS. 2A and 2B, the height reading hi provided by sensor $C_1$ at any point gives the height at which optics 28 will be positioned relative to wafer 22 after stage 34 has advanced the focal area in the scan direction by the distance D. In other words, taking y as the Y-coordinate of the center of focal area 50 along a given scan line, the height of the optics h(y) is given by:

$$h(y) = h_1(y-D) - [Z(y) - Z(y-D)] \quad (1)$$

Here Z(y) is the height setting of elevation stage 36 when the focal area is at location y along the Y-axis (which must be taken into account in interpreting the readings of the height sensor). The height h(y) given by equation (1) is used by controller 36 in order to drive stage 36 to the proper height for optimal focus at point y. When the scan line is scanned in the opposite direction, sensor $C_2$ and height reading $h_2$ are used instead.

Balanced control—The current height readings of the two sensors, $C_1$ and $C_2$, are both used in determining the height of the optics. For example, the height of the optics may be estimated as the arithmetic average of the two sensor readings:

$$h(y) = \tfrac{1}{2}[d_1(y) + h_2(y)] \quad (2)$$

This approach has the advantages of compensating for errors in flatness or tilt of translation stage 34, and of immunity to inaccuracies in reading the setting Z(y) of elevation stage 36 (as input to equation (1), for example). It requires, however, that a different control mode be used in edge regions 54 and 56, as described hereinbelow.

The averaging approach does not take into account local curvature of the wafer surface. For this purpose, a higher-order fit may be used, such as a spline interpolation:

$$h(y) = \frac{1}{2}[h_1(y-D) + h_2(y+D)] + \alpha D\left[\frac{\partial h_1(y-D)}{\partial y} - \frac{\partial h_2(y+D)}{\partial y}\right] \quad (3)$$

Here α is a weighting factor, which may be optimized for best interpolation results. Although the spline fit may give more accurate results than a linear average, it is more complicated to calculate and may be more sensitive to noise due to the derivative terms in equation (3). Alternatively, other higher-order approximations may be used, as will be apparent to those skilled in the art.

It can be seen in equations (1), (2) and (3) above that accurate determination of the height parameter h(y), and hence accurate adjustment of the optics, depends on accurate calibration of the sensor height readings $h_1$ and $h_2$. These readings are subject to a certain amount of DC drift. Furthermore, since the voltage generated by sensors 40 depends on capacitance measured by the sensors with respect to the wafer surface, there may be variations in the height readings due to the composition of the surface layers of the wafer. For example, the readings of sensors 40 may vary depending on whether the surface layer contains large amounts of metal or oxide. The relatively large footprint 52 of the sensors is useful in averaging over local variations in surface composition, but calibration of the sensors relative to the nature of the wafer surface that is under inspection is still useful in eliminating drift and material-dependent effects. The inventors have found that in the absence of such calibration, reading inaccuracy of up to about a few µm may occur.

In an embodiment of the present invention, the readings of height sense driver 42 are calibrated against an optimal optical focus of optics 28. The calibration procedure may be performed either on the actual wafer that is to be inspected or on a special reference wafer, which is similar in surface composition to the wafer that is to be inspected. System controller 44 drives stage 36 up and down, while detector 30 captures images of the wafer. This procedure is repeated until the system controller finds the Z-location of the wafer that gives the best optical focus. Typically, the best focus is considered to be that which gives the sharpest edges, or equivalently the highest contrast between bright and dark areas in the image. The voltage readings of sensors 40 are then measured at the Z-location of the optimal optical focus. These readings serve as the zero point for height readings and adjustment during subsequent inspection scans. In this manner, drift-related changes in the readings of sensors 40 are canceled out.

Figure 3:
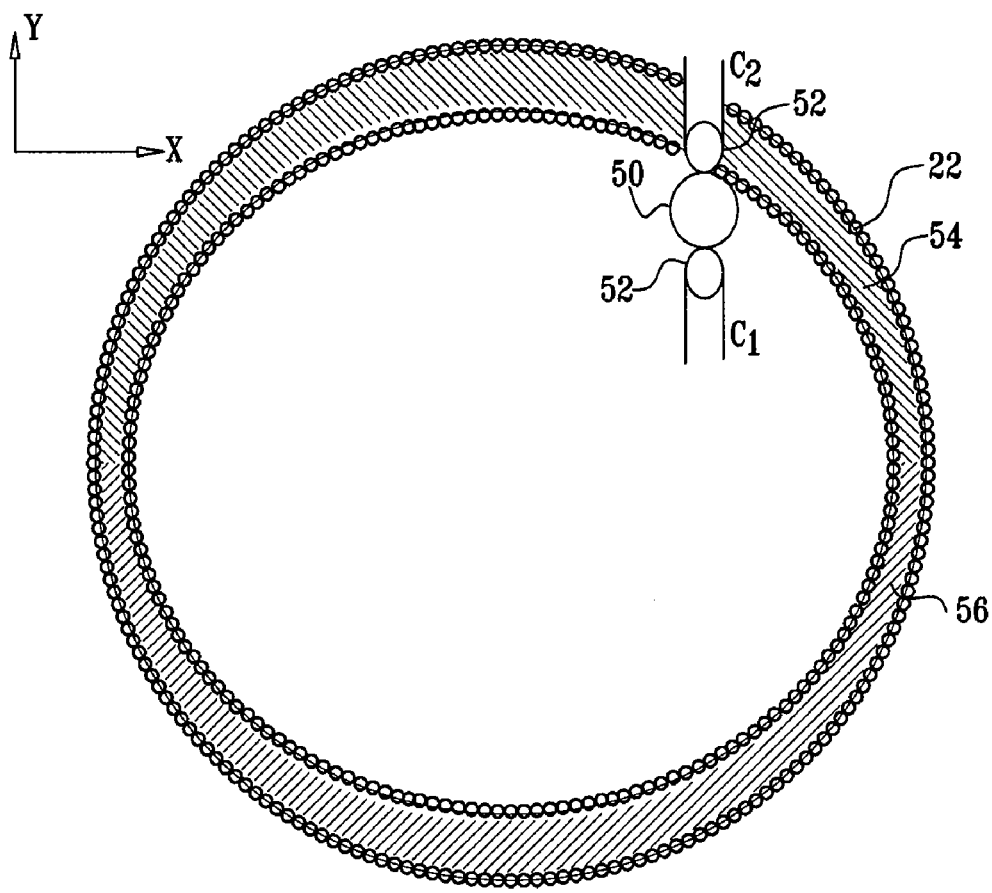
FIG. 3 is a schematic top view of a sample under inspection, showing regions near the edge of the sample in which a modified height sensing method is used, in accordance with an embodiment of the present invention.

FIG. 3 is a schematic top view of wafer 22, illustrating edge regions 54 and 56 in which the above-mentioned methods of operation are typically modified, in accordance with embodiments of the present invention. In this figure, the scan axis (Y-axis) is oriented in the vertical direction. Within region 54, in proximity to the edge of wafer 22, height sensor $C_2$ gives an invalid (or at least suspect) reading, while height sensor $C_1$ gives invalid or suspect readings in a region 56. Note that at the edges of the wafer along the X-axis (at the extreme left and right of the wafer), footprints 52 of both height sensors may extend over the edge of the wafer, so that neither sensor gives a valid reading. The difficulties of autofocus control in regions 54 and 56 are addressed by embodiments of the present invention that are described hereinbelow.

In order to describe the operation of autofocus mechanism 24 in regions 54 and 56, it is useful to distinguish between the following four situations:
(1) Beginning of scan line.
(2) End of scan line.
(3) Beginning of wafer scan.
(4) End of wafer scan.

It is assumed that at the beginning and end of each scan line, focal area 50 reaches (and typically passes) the edge of wafer 22. Thus, in the example shown in FIG. 3, if we assume the current scan line to be in the positive Y-direction (upward in this figure), focal area 50 and footprint 52 of at least sensor $C_1$ would have been off the lower edge of the wafer at the beginning of the scan line. When the scan reaches the end of the scan line, at least the footprint of sensor $C_2$ and focal area 50 will extend off the upper edge of the wafer. Assuming that the next scan line proceeds in the negative Y-direction, these relations will be reversed. At the beginning and end of the wafer scan (at the left and right sides of the wafer in FIG. 3), there may be scan lines for which the footprints of both $C_1$ and $C_2$ will overlap the edge of wafer 22, so that neither sensor will give a valid reading, as noted above.

When look-ahead control is used, as given by equation (1) above, footprint 52 of the look-ahead sensor ($C_2$ in the example of FIG. 3, assuming upward scanning) moves onto wafer 22 at the beginning of the scan line before focal area 50 moves onto the wafer. Therefore, the look-ahead sensor starts to provide valid readings of the sensor height ($d_2$ in the present example) before the actual optical image acquisition begins. Controller 38 places these readings of $h_2$ in a first-in-first-out (FIFO) buffer, according to the locations of the points at which the readings were taken. As soon as the first valid reading of $h_2$ is taken at the beginning of the scan line, controller 38 may drive stage 36 to adjust the Z-position of stage 36 accordingly. As a result, when focal area 50 moves onto the wafer a short time later, the focus will already be approximately correct. Once footprint 52 of $C_2$ has advanced by a distance D onto the wafer along the scan line, the FIFO buffer will be filled with entries, and the method of autofocus adjustment may proceed in accordance with equation (1), as described above. At the end of the scan line, look-ahead focus adjustment continues until there are no more valid height readings in the FIFO buffer, at which point the Z-position is locked until the next scan line.

When balanced control is used (according to equation (2) or (3), for example), the treatment of the beginning and end of scan lines is different. For the sake of simplicity, this treatment is described with reference to the arithmetic averaging approach (equation (2)), although it may be extended in a straightforward manner to higher-order height estimation procedures. As focal area 50 approaches the end of a given scan line, the last valid height reading from the leading sensor ($C_2$ in the example of FIG. 3, assuming upward scanning) is used to compute a height offset $h_{ofs}=(h_2^0-h_1^0)/2$, wherein $h_2^0$ is the last valid reading from the leading sensor and $h_1^0$ is the reading taken from $C_1$ at the time of reading $h_2^0$. As long as footprint 52 of $C_2$ is entirely or partly off wafer 22, the height parameter used by controller 38 is given by $h(y)=h_1(y)+h_{ofs}$, instead of the average height reading given by equation (2). This estimated input is used both at the end of one scan line and at the beginning of the subsequent scan line, before the $h_2(y)$ height reading becomes valid. When neither $C_1$ nor $C_2$ gives a valid reading, the Z-position of stage 36 is locked.

For scan lines at the beginning of a wafer scan, a pre-acquired estimate of the height reading of the look-ahead sensor (for look-ahead autofocus operation) or of both sensors (for balanced mode) may be used to set the Z-position of stage 36 when there is no valid height sensor reading for the scan line. To acquire these height estimates, stage 34 translates wafer 22 toward the center of the wafer so that detector assembly 27 and sensors 40 are located on a scan line that is closer to the center of the wafer. At this X-position, footprint 52 of at least one of sensors 40 is entirely on wafer 22. (For look-ahead control, it is sufficient that the footprint of the look-ahead sensor be on the wafer. For balanced control, it is desirable that the footprints of both sensors be on the wafer.) Controller 38 acquires and stores height readings from the sensors at the locations along this scan line. Stage 34 then translates the wafer to the scan slice starting position, so that the detector assembly can begin to scan from the starting edge of the wafer. At each position on the initial scan line or lines, as long as $C_1$ and $C_2$ do not give valid readings, controller 38 adjusts the height of stage 36 using the height readings measured at the nearest position on the pre-acquired scan line. Similarly, at the end of the wafer scan, controller 38 sets the height of stage 36 using the height readings taken at the nearest points along the preceding scan lines.

Figure 4:
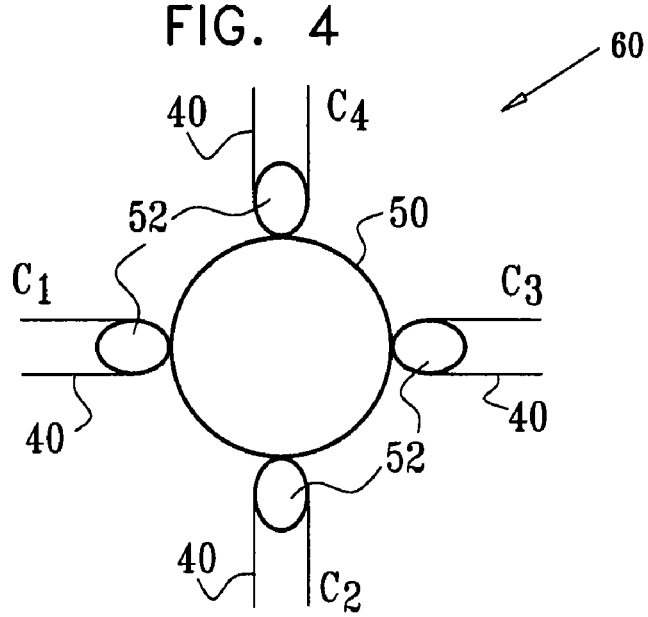
FIG. 4 is a schematic top view of a sample under inspection, showing an area of an image captured by an optical inspection system and adjacent height sensing areas, in accordance with another embodiment of the present invention.

FIG. 4 is a schematic top view of a sample under inspection, showing an alternative arrangement 60 of height sensors 40, in accordance with another embodiment of the present invention. In this embodiment, four height sensors, labeled $C_1$ through $C_4$ are arranged in pairs on opposite sides of a detector assembly (not shown in this figure), so that their footprints 52 surround focal area 50. The height sensor readings may be averaged to give a more accurate estimate of the height of the objective optics than in the dual-sensor embodiment shown above. Alternatively or additionally, the sensors may be used in a look-ahead mode to support scans along the X-axis, as well as the Y-axis. Other arrangements comprising more than two pairs of height sensors may also be used for such purposes and are considered to be within the scope of the present invention.

In an alternative embodiment, not shown in the figures, a single height sensor is positioned alongside the detector assembly, and makes height measurements in the look-ahead mode described above. In this embodiment, translation stage 34 is typically configured to scan all the lines of the raster pattern in the same direction, so that the height sensor is ahead of the detector assembly on all the scan lines. Alternatively, the detector assembly and height sensor may be rotated about the optical axis of the detector assembly so that the height sensor remains ahead of the detector assembly on all scan lines regardless of scanning direction.

As noted earlier, although the embodiments described above are directed to optical inspection of semiconductor wafers in a certain optical configuration, the principles of the present invention may similarly be applied to other optical inspection tasks and configurations and to different sorts of samples under inspection. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
   a detector configured to receive radiation from a focal area on a sample;
   a sensor, positioned in a known location relative to the detector along a translation path of the detector with respect to the sample; and
   a controller, adapted to determine an estimated height of the detector from the sample according to a height measured by the sensor from the sample at a site along the translation path but outside of the focal area.

2. The apparatus according to claim 1, further comprising means operative to adjust a focus of the detector responsively to the estimated height.

3. The apparatus according to claim 2, further comprising a second sensor positioned in a second known location relative to the detector and configured to measure a second estimated height relative to the sample at a second site outside of the focal area.

4. The apparatus according to claim 3, wherein the controller is operative to determine the estimated height responsively to the estimated height and the second estimated height.

5. A method, comprising determining an estimated height of a detector from a surface of a sample under inspection, the detector being configured to receive radiation from a focal area on said surface of said sample, said estimated height computed according to a measured distance between a sensor and said surface of said sample at a location outside of said focal area and along a translation path of said detector with respect to said sample.

6. The method according to claim 5, further comprising adjusting a focus of the detector responsively to the estimated height.

7. The method according to claim 6, further comprising tilting the sensor without blocking a collection angle of the detector with respect to the focal area.

8. The method according to claim 6, wherein said estimated height is further determined according to a second measured distance between a second sensor and said surface of said sample at a second locations outside of said focal area.

* * * * *